United States Patent [19]
Smith

[11] Patent Number: 5,576,006
[45] Date of Patent: Nov. 19, 1996

[54] ANTIMICROBIAL COMPLEXES

[75] Inventor: W. Novis Smith, Philadelphia, Pa.

[73] Assignee: W. Novis Smith and Co., Collingswood, N.J.

[21] Appl. No.: 311,151

[22] Filed: Sep. 23, 1994

Related U.S. Application Data

[63] Continuation-in-part of Ser. No. 750,425, Aug. 14, 1991, Pat. No. 5,399,343.

[51] Int. Cl.$^6$ ................................................. A01N 33/00
[52] U.S. Cl. ........................... 424/404; 424/43; 424/46; 424/76.2; 424/76.8; 36/44; 36/98
[58] Field of Search ....................... 424/404, 43, 46, 424/489, 76.2, 76.8; 36/36, 43, 44, 98; 523/122

[56] References Cited

U.S. PATENT DOCUMENTS

| | | | |
|---|---|---|---|
| 4,217,364 | 8/1980 | Kabara | 424/320 |
| 4,758,595 | 7/1988 | Ogunbiyi et al. | 514/635 |
| 4,877,605 | 10/1989 | Hendricks | 424/65 |
| 4,999,386 | 3/1991 | Oakes et al. | 523/122 |
| 5,049,383 | 9/1991 | Huth et al. | 424/405 |

*Primary Examiner*—Gollamudi S. Kishore
*Attorney, Agent, or Firm*—John Lezdey

[57] ABSTRACT

There is provided complexes of antifungal or antimicrobial compounds having at least one site which is a quaternary ammonium, amine, a mixture thereof, or the salts thereof. The complexes are useful in compositions for deodorizing and/or preventing the growth of odor causing microbes or fungus. The compositions are particularly useful for deodorizing footwear.

13 Claims, No Drawings

ANTIMICROBIAL COMPLEXES

RELATED APPLICATIONS

This application is a continuation-in-part of application Ser. No. 07/750,425 filed Aug. 14, 1991, now Pat. No. 5,399,343.

FIELD OF THE INVENTION

The present invention relates to novel complexes or antifungal or antimicrobial compounds or other functional compounds. More particularly, there is provided novel complexes which render the same antimicrobial activity as the unreacted smaller molecule but are less water soluble and more hypoallergenic. The complexes are especially useful in killing or deactivating odor causing microorganisms which are not absorbed by the skin.

BACKGROUND OF THE INVENTION

There is a need provide safe and effective means for preventing fungal and bacterial growth which can be used on or near a person's body without adverse effects on the user. There is a further need to provide preparations which will inhibit and/or prevent the growth of odor causing bacteria and fungus. The problem of odors from bacteria can be especially noticed in footwear, especially sneakers.

The problems found with using many antibacterial or antifungal agents are that such agents are irritating after prolonged contact or are quickly absorbed by stockings because they are water soluble.

Prior art solutions to sneaker and shoe odors was to use an absorbent such as charcoal or talc to absorb the moisture and to prevent the moisture and bacteria from collecting in the shoe or sneaker. However, such means required use of foot pads or powders which only temporarily reduced the accumulation of the odor causing elements.

Previously, hexachlorophene was widely used in many body preparations to kill bacteria on contact and to prevent growth of bacteria and fungus. Hexachlorophene was included in deodorant compositions, talcum preparations, foot powders, and the like. However, the hexachlorophene was used in direct contact with skin and was absorbable. Prolonged exposure to hexachlorophene was considered as being hazardous so that it was withdrawn from use in such compositions.

The bacteriostatic agents which are presently being utilized by the cosmetic industry such as 3-(trifluoromethyl)-4,4'-dichlorocarbanilide (IRGASAN) and 5-chloro-2-(2,4-dichlorophenoxy) phenol (IRGASAN DP-300) of Ciba-Geigy cannot be utilized in hypoallergenic formulations since there is the possibility of irritation over extended use. The compounds while insoluble in water and soluble in alkaline solutions and in organic solvents have no film forming capabilities so that they cannot be effectively utilized film forming formulations. Additionally, bacteriostatic agents merely prevent the growth of existing organisms and do not kill on contact new microorganisms which may be introduced into the compositions.

There is a need to provide hypoallergenic compositions which are used on or near body parts for preventing bacterial and fungal growth which does no adversely affect the user.

Japanese Patent Publication No. 1989-22824, which is herein incorporated by reference, discloses a medicament for external use that is fungicidal and exhibits an antibacterial spectrum. The medicament comprises quaternary ammonium salts of polymeric carboxylic acid compounds which are sparingly soluble in water. However, the active component is utilized for its ability to permeate into the cutaneous stratum corneum so that such use cannot be continuous and without medical supervision.

U.S. Pat. No. 4,332,763 to Hempel et al discloses the use of a quaternary ammonium polymer obtained by the reaction of dimethyl sulphate with a mixed polymer of vinyl pyrrolidone and dimethylamino ethylmethacrylate. However, the quaternary ammonium cation of this polymer is leachable and the polymer is slightly soluble so that polymer cannot be used in compositions which contact skin.

U.S. Pat. No. 3,872,128 to Byck, which is herein incorporated by reference, discloses anti-microbial ammonium polymer salts which are prepared from carboxyl-containing $\alpha$-olefin polymers and quaternary ammonium salts. The polymers are used to form solid polymeric articles for hospitals and patient care.

U.S. Pat. No. 3,404,134 to Rees, which is herein incorporated by reference discloses a process for crosslinking copolymers of alpha olefin and alpha, beta ethylenically unsaturated carboxylic acid units. The copolymers are crosslinked utilizing diamine cations. None of the diamine cations are stated as being anti-microbial. Furthermore, the polymers are used to make molded articles and sheet material.

It is understood that the term "polymer-quat" as used herein means polymers which are wholly or partially neutralized with biocidally active quaternary ammonium compounds or polyamine such as by ionic bonding or crosslinking whereby the biocidal activity of the quaternary ammonium compound or amine is maintained.

The term "body composition or preparation" used herein relates to powders, lotions, salves, or the like used in treating the body such as foot powders, talcum preparations, deodorant preparations, baby preparations and the like.

The term "polycarboxylic acid" is intended to mean carboxylic acid compounds having 2–4 carboxylic acid groups or anhydrides which reacted behave as polycarboxylic acids or salts thereof.

SUMMARY OF THE INVENTION

The invention provides novel antimicrobial complexes which are formed between polycarboxylic acids and functional biocides, fungicides, and microcides having at least one quaternary or amine site, or the salts thereof. The reactions between these functional compounds and the carboxylic acid causes at least one of quaternary ammonium or amine or combination of quaternary ammonium or amine molecules to coordinate or complex per molecule of polycarboxylic acid to form a more water insoluble higher molecule weight compound. These higher molecular weight species possess the full activity of the smaller unreacted functional molecule but are more resistant to being leached away and are more hypoallergenic. Preferably, the functional compound has two quaternary ammonium or amine sites or a mixture thereof. Advantageously, antimicrobial complexes are formed with antimicrobial biguanide compounds.

The invention also provides a method for reducing and/or eliminating odors caused by bacteria, especially in footwear such as shoes, sneakers and compositions thereof. The odor absorbent is preferably a basic compound such as an ammonium or alkali metal carbonate, bicarbonate, phosphate or perborate which are compatible with the complex.

DESCRIPTION OF THE PREFERRED EMBODIMENT

In accordance with the present invention there is provided novel complexes formed between polycarboxylic acids and functional biocides, fungicides, herbicides, pesticides, nematicides and microbicides, all having at least one site which is quaternary ammonium, amine, a mixture thereof, and/or the salts thereof.

The reaction between these functional or useful compounds containing the quaternary and/or amine site and polycarboxylic acid causes at least two functional molecules to coordinate or complex (react) per molecule of polycarboxylic acid. This forms a more insoluble higher molecular weight molecule. These higher molecular weight species possess the full activity of the smaller unreacted functional molecule but are more resistant to being washed away and are more hypoallergenic. They are more insoluble and longer lasting since the newly formed molecule has increased size. The formation of these simple but larger complexes or compounds has the effect of creating a slower release type of functional compound. Therefore, a larger lasting effect is achieved with these complexes without having to use the microbial or other type of biocidal agent or herbicide in higher doses or frequent doses.

Some of the factors involved in deodorizing footwear are the killing or deactivating odor causing bacteria and the treatment of footwear which through long use has the odor-causing components absorbed into the footwear material. When the compositions of the invention are used in new or odor-free footwear, there is prevented a buildup of odor causing components from bacteria or perspiration. However, in the well used footwear it is preferable to employ an odor absorbent or neutralizer such as a perborate, phosphate, carbonate or bicarbonate, most preferable are ammonium carbonate and ammonium bicarbonate which neutralize acidic odorants. A perfume can also be used. The complex can be formulated into a spray or powder by conventional methods.

A suitable liquid composition comprises:

about 1 to 10% by weight preferably about 2 to 5% of one or more complexes;

about 99 to 90% by weight of a solvent, preferably water, water-alkanol or alkanol. The preferred alkanols are the lower alkanols such as ethanol or isopropanol, and optionally, an odor absorbent.

Some of the factors which cause "diaper rash" or "diaper dermatitis" include ammonia, bacteria, pH, candida albicans and moisture. Urine in contact with enzymes and bacteria breaks down into ammonia and causes odor. It therefore appears that diaper rash control may be achieved to some degrees by eliminating or reducing the bacteria and enzymes which are present and those which promote the breakdown of urine. Accordingly, it is proposed to include in body preparations and powders which are intended for use on infants and individuals suffering from incontinence, the complexes of the invention in order to reduce and control the growth of the bacteria and enzymes which may be present. A suitable body powder for infants and for adults to control odor comprises 20 to 40 parts by weight of talc, about 20 to 40 parts by weight of a buffer, preferably sodium bicarbonate, about 10 to 20 parts by weight of complex and optionally, perfume.

Representative examples of suitable quaternary ammonium or amine based anti-fungal or anti-microbial agents and the salts thereof include methylbenezalkonium chloride, benzalkonium chloride, dodecyltrimethyl ammonium bromide, tetradecyltrimethyl ammonium bromide and hexadecyltrimethyl ammonium bromide. Tetramine compounds such as 1, 3, 5, 7-tetra-aza-adamantane hexamethylenetetramine, heterocyclic quaternary nitrogen-based anti-microbial agents include dodecylpyridinium chloride, tetradecylpyridinium chloride, cetylpyridinium chloride (CPC), N-alkyl pentamethyl propane diammonium dichloride, dicocodimethyl ammonium chloride, and pyridinium salts. Triazines such as DOWICIL (1, 3, 5-tris(2-hydroxyethyl) hexahydro-5-triazine) sold by Dow Corning Corporation, tetradecyl-4-methylpyridinium chloride and tetradecyl-4-methylpyridinium chloride, biguanides such as polyhexamethylene biguanide hydrochloride which is sold by ICI of Delaware under the trademark COSMICIL CQ.

Some anti-microbial silicone quaternary compounds sold by Dow Corning, may also be used. Other suitable anti-microbial agents which may be used are disclosed in Kirk-Othmer; *Encyclopedia of Chemical Technology*, 3rd Ed. Vol. 7, 1979, pp 793–832, which is incorporated herein by reference.

One or more complexes can be formulated into a composition of the invention to provide a variety of utilities or differences of solubility. That is, an antifungal complex can be formulated with an antimicrobial complex.

Polycarboxylic acids useful in the invention include: acrylic, carboxymethyl cellulose, methacrylic, ethacrylic, itaconic, maleic, fumaric, citric, oxalic, phthalic, tartaric, and the like. The salts thereof with anions such as citrates, tartrates, succinates, fumarates, maleates, malonates, malates, phthalates, etc. can be used. Maleic anhydride and other anhydrides are considered acids for the purposes of the present invention.

The complex with a polycarboxylic acid and quaternary ammonium compound of the invention can be generally prepared as follows:

A solution of the polycarboxylic acid in water or water-alcohol is formed either as the ammonium or sodium salt with ammonium or sodium hydroxide, respectively. The anti-microbial compound is dissolved in water or a water soluble solvent. The molecular ratio of anti-microbial compound to sodium or ammonium carboxylate groups in the acid or mixture of acids is adjusted to one or less than one by varying the quantity of solution to be added to the acid solution. The appropriate amounts of the two solutions are mixed with stirring. After about an hour the complex is separated. This complex can be added directly into spray compositions, powder compositions, etc. for control and the killing of microorganisms.

The following examples are illustrative of the invention but are not to be construed as to limiting the scope thereof in any manner. The percentages disclosed herein relate to percentages by weight unless otherwise stated.

EXAMPLE 1

Preparation of COSMOCIL and citrate complex.

12 g of diammonium citrate is dissolved in 88 g of deionized water. The solution is added dropwise to 225 g of COSMOCIL CQ (20%) containing 3 drops of Triton CF-10 dispersing aid. The concentration is about 13.8%. 138g of sodium bicarbonate is dissolved in 1587 g of water and then added to the solution of the complex. This solution contains about 1.9% of active complex.

The solution when sprayed on a clear surface deposits a clear film which is active against bacteria and shoe odor.

EXAMPLE 2

Preparation of DOWCIL and sodium carboxymethyl cellulose complex:

A. 12 g of Aqualon sodium carboxymethyl cellulose no. 7L from Hercules was dissolved in 290 g of deionized water to form a 3% solution of sodium carboxymethyl cellulose.

B. 2.6 g of DOWCIL 200 was dissolved in 7.4 g of deionized water and added to the solution of part A to form a clear solution containing about 1.9% active complex.

C. 9 g of sodium bicarbonate was added to the solution of active complex of Part B. A clear yellow solution formed which was active against bacteria and shoe odor.

In lieu of sodium bicarbonate, ammonium bicarbonate, carbonate perborate or phosphate may be used. Other complex anions in lieu of the citrate may be used including tartrate, succinate, fumarate, maleate, malonate, malate, phthalate, etc.

EXAMPLE 3

| BODY POWDER OR BABY POWDER | |
| --- | --- |
| Ingredient | % by weight |
| Talc | 40 |
| Sodium bicarbonate | 40 |
| Complex of Example 1 | 20 |

As a body powder the composition is effective to deactivate or kill odor causing bacteria. As a baby powder the sodium bicarbonate neutralizes the pH of urine and the complex kills the odor causing bacteria in the urine.

EXAMPLE 4

A solution of Adogen 477 (a diquaternary chloride) in water was added to an aqueous solution of low molecular weight polyacrylic acid (as a ammonium salt) with vigorous stirring. The molecular amount of anti-microbial was approximately 0.8 ratio to the amount of neutralized carboxyl groups present in the polymer. The precipitate was filtered and dried. It was useful as a anti-microbial formulating agent.

EXAMPLE 5

A solution of low molecular weight polyacrylic acid was added to a solution of BIOBAN P-1487. About 4% of a 5% solution of calcium chloride was then added to ensure total precipitation and insolubilization of the complex. The molecular amount of anti-microbial was approximately 0.8 ratio to the amount of neutralized carboxyl groups present. The precipitate was recovered and used as an anti-microbial agent in the film forming formulations.

What is claimed is:

1. A method for deodorizing or reducing odors in footwear which comprises treating footwear with a composition in the form of a spray comprising an antifungal, biocidal or antimicrobial film forming complex of a polycarboxylic acid and a functional antimicrobial, biocidal or antifungal compound having at least one site which is quaternary ammonium, amine, a mixture thereof or the salts thereof, said film forming complex being the reaction product of said functional compound and a polycarboxylic acid wherein at least two functional molecules complex or coordinate per molecule of polycarboxylic acid.

2. A method for deodorizing or reducing odors in footwear which comprises treating footwear with a composition comprising an effective amount of a film forming complex of a polycarboxylic acid and a functional antimicrobial, biocidal or antifungal biguanide compound or the salts thereof, said film forming complex being the reaction product of said functional compound and a polycarboxylic acid wherein at least two functional molecules complex or coordinate per molecule of polycarboxylic acid.

3. The method of claim 2 wherein said biguanide is a polyhexamethylene biguanide hydrochloride.

4. The method of claim 1 wherein said antimicrobial compound is a triazine.

5. The method of claim 4 wherein said triazine is 1, 3, 5-tris (2-hydroxylethyl) hexahydro-5-triazine.

6. The method of claim 1 wherein said antimicrobial agent is a tetramine.

7. The method of claim 6 wherein said tetramine is 1, 3, 5, 7-tetra-aza-adamantane hexamethylenetetramine.

8. The method of claim 6 wherein said tetramine is 1-(3-chloroallyl) -3, 5, 7-triaza-1-azonia adamantane.

9. The method of claim 2 wherein said complex is a complex of a polycarboxylic acid having 2–4 carbon atoms and an antimicrobial compound which is a biguanide.

10. The method of claim 9 wherein said polycarboxylic acid is citric acid and said biguanide is polyhexamethylene biguanide acid addition salt.

11. The method of claim 2 wherein said composition includes an odor absorbent.

12. The method of claim 11 wherein said odor absorbent is ammonium carbonate or ammonium bicarbonate.

13. The method of claim 2 wherein said composition includes a perfume.

* * * * *